(12) United States Patent
Bonner et al.

(10) Patent No.: US 6,248,877 B1
(45) Date of Patent: Jun. 19, 2001

(54) SOLID PHASE SYNTHESIS OF ORGANIC COMPOUNDS VIA PHOSPHITYLATING REAGENTS

(75) Inventors: Alex G. Bonner, Lexington; Lawrence S. Udell, Brookline, both of MA (US)

(73) Assignee: Biolink Partners, Watertown, MA (US)

( * ) Notice: Subject to any disclaimer, the term of this patent is extended or adjusted under 35 U.S.C. 154(b) by 0 days.

(21) Appl. No.: 09/287,076

(22) Filed: Apr. 6, 1999

Related U.S. Application Data

(60) Provisional application No. 60/080,993, filed on Apr. 7, 1998.

(51) Int. Cl.[7] .................... C07H 19/00; C07H 21/00; C07H 21/02; C07H 21/04
(52) U.S. Cl. ................. 536/25.3; 536/22.1; 536/23.1; 536/24.3; 536/25.33
(58) Field of Search ................ 536/22.1, 23.1, 536/24.3, 25.3, 25.33

(56) References Cited

U.S. PATENT DOCUMENTS

| 5,512,668 | * | 4/1996 | Stec et al. | 536/25.33 |
| 5,571,937 | | 11/1996 | Watanabe et al. | 560/147 |

FOREIGN PATENT DOCUMENTS

WO 86/07362  12/1986  (WO).
WO 90/03382  4/1990  (WO).

OTHER PUBLICATIONS

Beaucage et al. "Advances in the synthesis of oligonucleotides by the phosphoramidite approach" Tetrahedron, vol. 48, No:12m pp. 2223–2311, 1992.*

Uhlmann et al. "Antisense Oligonucleotides: A new therapeutic principle" Chemical Reviews, vol. 90, No: 4, pp. 543–584, 1992.*

Sinha et al. "Polymer support oligonucleotide synthesis XVII: use of beta–cyanoethyl–N, N–dialkylamino–/N–morpho lino phosphoramidite of deoxynucleosides for the synthesis of DNA fragments simplifying deprotection and isolation of the final product" Nucleic Acids Research, 12(11):4539–4557 (1984).

Zhang et al. "A novel phosphitylating reagent for in situ generation of deoxyribunocleoside phosphoramidites" Tetrahedron, 37(3):331–334 (1996).

* cited by examiner

Primary Examiner—Jezia Riley
(74) Attorney, Agent, or Firm—Lahive & Cockfield, LLP; Giulio A. DeConti, Jr.; Nicholas P. Triano, III

(57) ABSTRACT

Methods for preparing organic compounds, such as oligonucleotides, on solid supports are described. Libraries of the compounds and methods of using the compounds are also disclosed.

26 Claims, 11 Drawing Sheets

SEQUENCE LISTING

<160> NUMBER OF SEQ ID NOS: 2

<210> SEQ ID NO 1
<211> LENGTH: 22
<212> TYPE: DNA
<213> ORGANISM: synthetic construct

<400> SEQUENCE: 1
tgtcagtgac tgtgaattcg ct                                              22

<210> SEQ ID NO 2
<211> LENGTH: 22
<212> TYPE: DNA
<213> ORGANISM: synthetic construct

<400> SEQUENCE: 2
agcgaattca cagtcactga ca                                              22

SOLID PHASE SYNTHESIS OF ORGANIC COMPOUNDS VIA PHOSPHITYLATING REAGENTS

RELATED APPLICATIONS

This application claims the benefit of priority under 35 U.S.C. 119(e) to U.S. Provisional application Ser. No. 60/080,993, filed on Apr. 7, 1998, the entire contents of which are incorporated herein by reference.

BACKGROUND OF THE INVENTION

The synthesis and screening of small molecule combinatorial libraries has become an important new technology for drug discovery. (For reviews see: (a) Gallop, M. A.; Barrett, R. W.; Dower, W. J.; Fodor, S. P. A.; Gordon, E. M. *J. Med. Chem.* 1994, 37, 1233. (b) Gordon, E. M.; Barrett, R. W.; Dower, W. J.; Fodor, S. P. A.; Gallop, M. A. *J. Med. Chem.* 1994, 37, 1385. (c) Moos, W. H.; Green, G. D.; Pavia, M. R. Recent Advances in Generation of Molecular Diversity. in *Annual Reports in Medicinal Chemistry;* Bristol, J. A., Ed.; Academic Press, Inc.; San Diego, Calif., 1993; Vol. 28, pp. 315–324. (d) Ecker, D. J.; Crooke, S. T. *Biotechnology* 1995, 13, 351. (e) Terrett, N. K.; Gardner, M.; Gordon, D. W.; Kobylecki, R. J.; Steele J. Tetrahedron 1995, 51, 8135. (f) Thompson, L. A.; Ellman, J. A. *Chem. Rev.* 1996, 96, 555. (g) Herkens, P. H. H.; Ottenheijm, H. C. J.; Rees, D. Tetrahedron, 1996, 52, 4527. (h) Fruchtel, J. S.; Jung, G. *Angew. Chem. Int. Ed. Engl.* 1996, 35, 17.) A convenient format for the generation of these libraries is synthesis of organic compounds on a solid phase. Solid phase synthesis is especially useful for reactions where excess reagents can be used to drive the reactions to completion. The excess reagents and soluble byproducts can be easily removed. (See, for example: (a) Kurth, M. J.; Randall, L. A. A.; Chen, C.; Melander, C.; Miller, R. B. *J. Org. Chem.* 1994, 59, 5862. (b) Hiroshige, M.; Hauske, J. R.; Zhou, P. J. *Am. Chem. Soc.* 1995, 117, 11590. (c) Wipf, P.; Cunningham, A. *Tetrahedron Lett.* 1995, 36, 7819. (d) Goff, D. A.; Zuckermann, R. N. *J. Org. Chem.* 1995, 60, 5744. (e) Plunkett, M. J.; Ellman, J. A. *J. Org. Chem.* 1995, 60, 6006. (f) Kick, E. K.; Ellman, J. A. *J. Med. Chem.* 1995, 38, 1427. (g) Forman, F. W.; Sucholeiki, I. *J. Org. Chem.* 1995, 60, 523. a) Holmes, C. P.; Jones, D. G. *J. Org. Chem.* 1995, 60, 2318. (i) Holmes, C. P.; Chinn, J. P.; Look, G. C.; Gordon, E. M.; Gallop, M. A. *J. Org. Chem.* 1995, 60, 7328.) Another important feature of solid phase synthesis is allowing "split and combine" methodology to be employed for library construction. Thus, generating diverse combinatorial libraries requires the development of solid phase syntheses of biologically active molecules on solid support, and the exploration of such synthetic methodologies for preparation of libraries.

Often compounds isolated from natural products have biological activity. For example, derivatives prepared from natural products, nucleic acids, peptides, proteins, and mimics thereof have remarkable biological activities. (See: Boyd, G. V. In *Comprehensive Heterocyclic Chemistry,* Vol. 6; Part 4B, Katritzky, A. R.; Rees, C. W., Eds.; Pergammon: Oxford, 1984; p178.)

Preparation of high molecular weight organic compounds, such as, for example, oligonucleotides, can be synthetically challenging. Often multiple synthetic steps are required to prepare the desired compounds. As a consequence of multistep syntheses, reaction conditions utilized to form oligonucleotides can facilitate degradation of the remaining molecular functionality. Additionally, synthetic manipulation of an oligonucleotide can cause the oligonucleotide to fragment into shorter lower molecular weight portions, thereby reducing the yield of the desired compound.

SUMMARY OF THE INVENTION

The present invention is directed to methods for preparing organic compounds, such as oligonucleotides, via solid phase synthesis.

In one aspect, the invention provides methods, e.g., automated methods, for preparing organic compounds. The methods include combining a substrate having a reactive nucleophilic group and a nucleophilic group protected by a removable protecting group, with a phosphitylating agent, thereby forming an in situ phosphitylated substrate. The in situ phosphitylated substrate is combined with a functionalized support, such that an in situ phosphitylated substrate is bound to the support, thereby forming a support bound phosphitylated substrate.

The method can further include treating the support bound phosphitylated substrate to selectively remove the protecting group from the protected nucleophilic group, thereby forming a support bound phosphitylated substrate bearing a reactive nucleophilic group. Thereafter, the support bound phosphitylated substrate bearing a reactive nucleophilic group can be combined with an in situ formed phosphitylated substrate, such that a support bound phosphitylated substrate bearing a reactive nucleophilic group is formed.

The support bound phosphitylated substrate can be treated to selectively remove the protecting group from the protected nucleophilic group, thereby forming a support bound phosphitylated substrate bearing a reactive nucleophilic group. The aforementioned steps can be repeated until a product formed of a plurality of substrates is obtained. The methods further provide that the product can be cleaved from the support and that optionally, the final deprotection step can be omitted.

In another aspect, the invention provides methods, e.g., automated, for preparing organic compounds, such as oligonucleotides. The methods include treating a support with a phosphitylating agent, thereby forming an a catena phosphitylated support and treating the a catena phosphitylated support with a substrate having a reactive nucleophilic group and a nucleophilic group protected by a removable protecting group, thereby forming a support bound phosphitylated substrate bearing a protecting group. The methods of the invention can further include removal of the protecting group from the support bound phosphitylated substrate, thereby forming a support bound phosphitylated substrate bearing a reactive nucleophilic group.

A substrate having a reactive nucleophilic group and a nucleophilic group protected by a removable protecting group can be combined with a phosphitylating agent, thereby forming an in situ phosphitylated substrate The in situ phosphitylated substrate can then be combined with the phosphitylated substrate bearing a hydroxyl functionality, thereby forming a support bound phosphitylated substrate bearing a protecting group. The protecting group can be removed from the support bound phosphitylated substrate, thereby forming a support bound phosphitylated substrate bearing a reactive nucleophilic group.

Alternatively, the methods of the invention include treating the support bound phosphitylated substrate bearing a reactive nucleophilic group with a phosphitylating agent, thereby forming a phosphitylated support bound substrate. The phosphitylated support bound substrate is then treated with a substrate having a reactive nucleophilic group and a nucleophilic group protected by a removable protecting group, thereby forming a support bound phosphitylated substrate bearing a protecting group. The protecting group is then removed from the support bound phosphitylated substrate, thereby forming a support bound phosphitylated substrate bearing a reactive nucleophilic group.

Optionally, the aforementioned steps can be repeated until a product formed of a plurality of substrates is obtained. The methods of the invention further provide that the product can be cleaved from the support and that optionally, the final step deprotection step can be omitted.

Optionally, the methods of the invention can include more than one substrate having a reactive nucleophilic group and a nucleophilic group protected by a removable protecting group or that more than one substrate can be included which is have a plurality of reactive nucleophilic groups and a plurality of nucleophilic groups protected by removable protecting groups. Moreover, the methods of the invention can include the step of capping failure substrates by reacting a capping agent with reactive nucleophilic groups of failure substrates.

The methods of the invention include the phosphitylating agent having the formula:

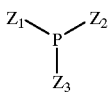

wherein one of $Z_1$, $Z_2$ and $Z_3$ is displaced by said reactive nucleophilic group of the substrate. One example of a phosphitylating agent is where $Z_1$ is chlorine, $Z_2$ is an N,N-dimethylamino, diethylamino, diisopropylamino, or N-morpholino group and $Z_3$ is a β-cyanoethyl group. The methods of the invention can further include the step of oxidizing at least one support bound phosphitylated substrate with formation of a pentavalent phosphorous group, such as a phosphotriester.

Suitable substrates for the present invention include organic moieties having reactive nucleophilic groups such as hydroxyl groups, amino groups and sulfur groups, e.g., thiols. Examples of substrates which include reactive nucleophilic groups include diols, triols, polyols, diamines, triamines, polyamines, aminoalcohols, polyaminoalcohols, dithiols, trithiols, polythiols, hydroxythiols, aminothiols, etc. Preferred substrates are oligonucleotides.

Generally, the substrate includes two nucleophilic groups; one is a reactive nucleophilic group, e.g., unprotected, and one is an unreactive nucleophilic group protected by a removable protecting group, such as a dimethoxytrityl group. Optionally, the substrate can include more than one reactive nucleophilic group and more than one protected nucleophilic group.

In still another aspect, the invention provides products produced from the methods of the invention.

DETAILED DESCRIPTION OF THE INVENTION

Figure 1:
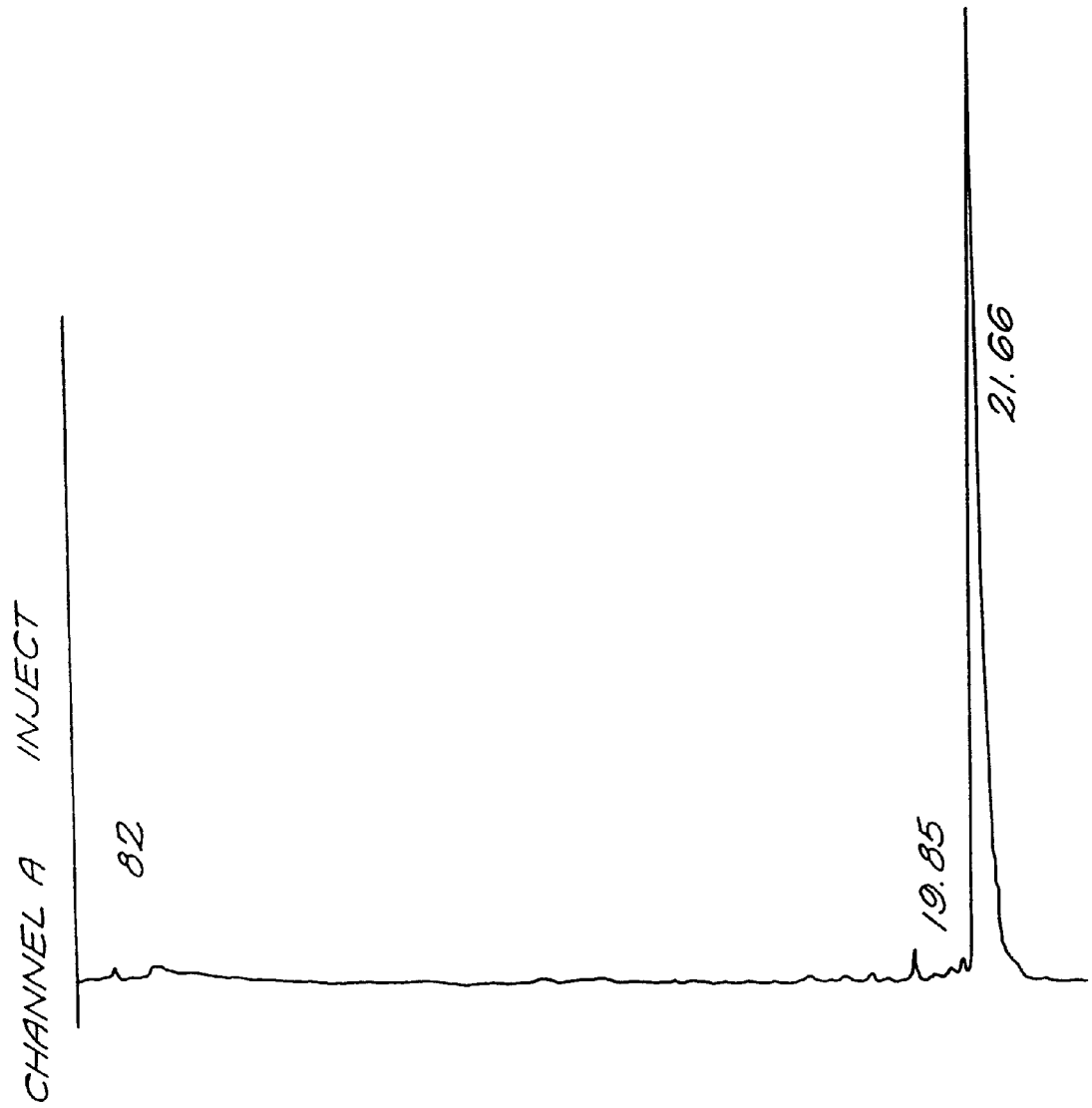
FIG. 1 is an anion exchange chromatogram of a $C_{22}$ oligonucleotide made using conventional DNA synthesis chemistry, as detailed in Example 3.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The invention relates to methods, e.g., automated methods, of preparing organic compounds, such as oligonucleotides, via phosphitylating agents.

In one embodiment, the invention pertains to methods, e.g., automated methods, for preparing organic compounds. The methods include combining a substrate having a reactive nucleophilic group and a nucleophilic group protected by a removable protecting group, with a phosphitylating agent, thereby forming an in situ phosphitylated substrate. The in situ phosphitylated substrate is combined with a functionalized support, such that an in situ phosphitylated substrate is bound to the support, thereby forming a support bound phosphitylated substrate.

The method can further include treating the support bound phosphitylated substrate to selectively remove the protecting group from the protected nucleophilic group, thereby forming a support bound phosphitylated substrate bearing a reactive nucleophilic group. Thereafter, the support bound phosphitylated substrate bearing a reactive nucleophilic group can be combined with an in situ formed phosphitylated substrate, such that a support bound phosphitylated substrate bearing a reactive nucleophilic group is formed.

The support bound phosphitylated substrate can be treated to selectively remove the protecting group from the protected nucleophilic group, thereby forming a support bound phosphitylated substrate bearing a reactive nucleophilic group. The aforementioned steps can be repeated until a product formed of a plurality of substrates is obtained. The methods further provide that the product can be cleaved from the support and that optionally, the final deprotection step can be omitted.

In another aspect, the invention provides methods, e.g., automated, for preparing organic compounds, such as oligonucleotides. The methods include treating a support with a phosphitylating agent, thereby forming an a catena phosphitylated support and treating the a catena phosphitylated support with a substrate having a reactive nucleophilic group and a nucleophilic group protected by a removable protecting group, thereby forming a support bound phosphitylated substrate bearing a protecting group. The methods of the invention can further include removal of the protecting group from the support bound phosphitylated substrate, thereby forming a support bound phosphitylated substrate bearing a reactive nucleophilic group.

A substrate having a reactive nucleophilic group and a nucleophilic group protected by a removable protecting group can be combined with a phosphitylating agent, thereby forming an in situ phosphitylated substrate The in situ phosphitylated substrate can then be combined with the phosphitylated substrate bearing a hydroxyl functionality, thereby forming a support bound phosphitylated substrate bearing a protecting group. The protecting group can be removed from the support bound phosphitylated substrate, thereby forming a support bound phosphitylated substrate bearing a reactive nucleophilic group.

Alternatively, the methods of the invention include treating the support bound phosphitylated substrate bearing a reactive nucleophilic group with a phosphitylating agent, thereby forming a phosphitylated support bound substrate. The phosphitylated support bound substrate is then treated with a substrate having a reactive nucleophilic group and a nucleophilic group protected by a removable protecting group, thereby forming a support bound phosphitylated substrate bearing a protecting group. The protecting group is then removed from the support bound phosphitylated substrate, thereby forming a support bound phosphitylated substrate bearing a reactive nucleophilic group.

Optionally, the aforementioned steps can be repeated until a product formed of a plurality of substrates is obtained. The methods of the invention further provide that the product can be cleaved from the support and that optionally, the final step deprotection step can be omitted.

Optionally, the methods of the invention can include more than one substrate having a reactive nucleophilic group and a nucleophilic group protected by a removable protecting group or that more than one substrate can be included which have a plurality of reactive nucleophilic groups and a plurality of nucleophilic groups protected by removable protecting groups. Moreover, the methods of the invention can include the step of capping failure substrates by reacting a capping agent with reactive nucleophilic groups of failure substrates.

The term "automated" is art recognized and is intended to include those methods by which an instrument is utilized to combine reagents in a stepwise fashion, thereby eliminating, in whole or in part, the need for an individual to mix or add reagents to each other. The term is further intended to include those purification steps and washing steps which are often required during the synthesis of organic compounds. The instrument is capable of performing these steps, as well as others, by programming, for example. For example, commercially available automated peptide synthesizers (e.g., Milligen/Biosearch 9600) can be adapted to prepare the compounds of interest with modifications to or addition of software instructing the instrument what reagents to add in a specified order.

The term "substrate" is intended to include organic moieties having functional groups appended thereto. Suitable substrates for the present invention include organic moieties having reactive nucleophilic groups such as hydroxyl groups, amino groups and sulfur groups, e.g., thiols. Examples of substrates which include reactive nucleophilic groups include diols, triols, polyols, diamines, triamines, polyamines, aminoalcohols, polyaminoalcohols, dithiols, trithiols, polythiols, hydroxythiols, aminothiols, etc.

Preferred substrates of the invention are oligonucleotides. One advantage this invention provides is the ability to construct oligonucleotides from "blocks" of smaller oligonucleotide fragments. Other preferred substrates of the invention include nucleosides having a protected 5' hydroxyl group and an unprotected 3' hydroxyl group. In a preferred embodiment, the 5' hydroxyl is protected with a dimethoxytrityl group. Additionally, preferred substrates of the invention include nucleosides having a 3' hydroxyl group and an unprotected 5' hydroxyl group, wherein 3' hydroxyl is protected with a dimethoxytrityl group.

Generally, the substrate includes two nucleophilic groups; one is a reactive nucleophilic group, e.g., unprotected, and one is an unreactive nucleophilic group protected by a removable protecting group, such as a dimethoxytrityl group. Optionally, the substrate can include more than one reactive nucleophilic group and more than one protected nucleophilic group.

The substrates can include additional functionality other than nucleophilic groups. Typically the substrates of interest are alkyl or aryl based.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 or fewer. Likewise, preferred cycloalkyls have from 4–10 carbon atoms in their ring structure, and more preferably have 5, 6 or 7 carbons in the ring structure.

The term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)).

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles", "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" refers to unsaturated aliphatic groups analogous in length and possible substitution to the alkyl groups described above, but that contain at least one double bond.

The terms "alkoxyalkyl" and "thioalkoxyalkyl" refer to alkyl groups, as described above, which further include oxygen or sulfur atoms replacing one or more carbons of the hydrocarbon backbone, e.g., catenary oxygen or sulfur atoms.

Unless the number of carbons is otherwise specified, "lower alkyl" as used herein means an alkyl group, as defined above, but having from one to ten carbons, more preferably from one to six carbon atoms in its backbone structure. Preferred alkyl groups are lower alkyls having one to three carbon atoms.

The terms "heterocyclyl" or "heterocyclic radical" refer to the radical of 3- to 10-membered ring structures, more preferably 4 to 7-membered rings, which ring structures include one to four heteroatoms. Heterocyclyl groups include pyrrolidine, oxolane, thiolane, oxazole, piperidine, piperazine, morpholine, lactones, lactams such as azetidinones and pyrrolidinones, lactones, sultams, sultones, and the like. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. A heteroalkyl moiety is an alkyl substituted with a heteroaromatic group.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" as used herein means an atom of any element other than carbon or hydrogen. Preferred heteroatoms are nitrogen, oxygen, sulfur and phosphorus.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be is obtained in substantially pure form by classical separation techniques and by stereochemically controlled synthesis.

The term "substantially pure," as used herein, refers to a compound which is substantially free of impurities, including (but not limited to) starting materials, side products, and the like. A compound is "substantially pure" if it comprises at least about 80%, more preferably 90%, still more preferably at least about 95% of the composition. If a single isomer of a compound is desired (e.g., a single diastereomer, enantiomer, or regioisomer), the compound is preferably substantially free of any undesired isomers (e.g., the unwanted enantiomer, diastereomers, or regioisomers), i.e., the desired isomer comprises at least about 80%, more preferably 90%, still more preferably at least about 95% of the weight of the isomers present in the composition.

The term "reactive nucleophilic group" is intended to include those groups which have nucleophilic character, e.g., primary, secondary and tertiary amines, thiols, and hydroxyl groups and their anions. These reactive nucleophilic groups can displace leaving groups attached to a phosphitylating agent.

The term "removable protecting group" is intended to include those groups which protect an organic functionality, such as a nucleophilic group, under select reaction conditions without removal of the group and yet which can be removed under appropriate reaction conditions without affecting other functionalities present in the molecule, e.g., hydrolysis or degradation of the molecule. A preferred protecting group for hydroxyl groups is the dimethoxytrityl group. Dimethoxytrityl groups can be removed under conditions known to those skilled in the art.

The term "phosphitylating agent" is intended to include those compounds having the formula

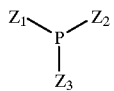

wherein one of $Z_1$, $Z_2$ and $Z_3$ is displaced by said reactive nucleophilic group of the substrate. $Z_1$, $Z_2$ and $Z_3$ are suitable groups which are displace by a reactive nucleophilic group of a substrate molecule and include alkoxides, halides, alkylamines and combinations thereof. One example of a phosphitylating agent is where $Z_1$ is chlorine, $Z_2$ is an N,N-dimethylamino, diethylamino, diisopropylamino, or N-morpholino group and $Z_3$ is a β-cyanoethyl group.

The term "in situ" is art recognized and is intended to include those reactions between reactive species which are not isolated and purified prior to a subsequent step. Preferably in situ reactions included in the methods of the invention are performed in solution, e.g., in the presence of organic solvents.

The term "phosphitylated substrate" is intended to include those substrates, as described above, which have undergone reaction with a phosphitylating agent, thereby forming a phosphitylated derivative thereof.

The term "solid support" is known in the art and, as used herein, refers to a solid or insoluble material suitable for solid phase synthesis of the compounds of the invention. The solid support can be a particle such as a bead, or a surface, such as a chip or wafer. In general, a solid support will be an inorganic or polymeric organic matrix, such as are known in the art. A variety of solid supports are known in the art (for examples, see, e.g., M. Bodansky "Principles of Peptide Synthesis", 2nd edition, Springer-Verlag, Berlin (1993); Hauske, J. R.; Dorff, P. Tetrahedron Lett. 1995, 36, 1589; and references cited therein). Many such art-recognized solid supports are useful in the methods of the invention. For example, solid supports suitable for use in the present invention include suitably modified forms of: silica (e.g., particles such as silica gel), silicon (e.g., wafers or chips), glass (e.g., a glass plate or controlled pore glass beads), polystyrene, polystyrene/divinylbenzene copolymer, polyacrylamide, Tenta-Gel, Wang resin, Rapp resin, Merrifield resin, Rink resin, and the like.

The term "functionalized" solid support, " as used herein, refers to a polymeric resin which has been functionalized with a reagent, an activating agent, to be reactive to linker molecules. For example, treatment of a solid support containing hydroxyl functionality with carbonyldiimidazole (CDI) or a trialkoxy 3-aminopropylsilane derivative forms an activated solid support which is functionalized. The surface of the solid support is thereby rendered reactive to certain types of nucleophilic molecules, such as diamines or dihalides, which are linkers.

The term "linker group," as used herein, refers to a linking or spacing moiety which can be used to covalently or non-covalently link a compound to a solid support. The linker group can include the reaction product of an activated resin and a molecule, a linker, which has reacted with the activated resin and still retains functionality which can be further reacted. The linker group can further include the reaction product between an activated solid phase bound linker and a reactive molecule, such as a dicarboxylic add anhydride or an amino acid in the presence of a coupling reagent. This reaction product, the linker group can include functionality which can then be further reacted with additional species. This process of reacting a solid phase bound linker and a reactive molecule can be repeated, thereby forming a linker group which contains several linkers and reactive molecules. Linker groups suitable for use in the invention are known in the art for use in solid-phase synthesis.

The term "linker, " as used herein refers to a molecule which reacts with a solid support treated with an activation agent, an activated resin or solid support, and still retains functionality within the molecule which can further react with another reactive molecule. It will be appreciated by the skilled artisan that a variety of linkers can be used to covalently (or, in certain embodiments, non-covalently) tether the compounds of the invention to a solid support. Linkers can be selected according to criteria such as length, chemical stability (or lability, where it is desired to cleave the compound from the resin), and the like.

Linker groups useful for immobilizing compounds on a solid support are well known in the art and include, e.g., diamino linkers, phenylene moieties, and the like. A particularly preferred linker group is the linker group described in Hauske, J. R.; Dorff, P. Tetrahedron Lett. 1995, 36, 1589. This linker group, the reaction product between an CDI activated solid support and a diamine, is easily synthesized, stable under a variety of reaction conditions, and readily cleaved to release the product from the solid support.

A particularly preferred linker group of the present invention is the reaction product between a diamine treated activated solid support and a dicarboxylic acid anhydride or an amino acid with a coupling reagent. This linker group therefore contains functionality which can be synthetically modified. After synthetic modifications have been completed, the linker group, or a portion of the linker group can be cleaved to release the product from the solid support.

It will be understood that the linker can be selected to have a length which permits facile reaction with a substrate compound immobilized on a solid support. For example, the linker should be long enough to avoid steric encumbrance of the immobilized compound by the solid support. The linker can be selected to be cleavable under a variety of conditions (e.g., hydrolytic, nucleophilic, electrolytic, oxidative, photolytic, and the like), if desired, as is known in the art. The skilled artisan will appreciate that the choice of linker, in combination with the choice of solid support, can influence factors such as reaction time, completeness of reaction, releasability of the reaction products, and the like. Thus, the linker and solid support will in general be selected to permit ready immobilization, reaction, isolation, and purification of the compounds of the invention.

The term "capping agent" is art recognized and is intended to include those agents which are used to react or block with functional groups which remain after a reaction step, e.g., nucleophiles which have not reacted with an electrophilic agent such as a phosphitylating agent. Typical capping or blocking agents include dialkylphosphites, arylisocyanates, diethoxytriazolylphospine, etc.

The term "a catena" is intended to include those reactions which are conducted on the solid support, such as phosphitylation of the support. The phosphitylated support can then undergo nucleophilic reactions with substrates which include reactive nucleophiles. In this sense the substrates are attached and grown from the support.

Standard techniques for in situ chemical synthesis of peptides are known in the art. For example, peptides and oligonucleotides can be synthesized by coupling protocols. Automated peptide synthesizers are commercially available (e.g., Milligen/Biosearch 9600) and can be adapted for synthesis of, for example, oligonucleotides. To create degenerate positions within oligonucleotides of a synthetic library, two approaches can be used. A preferred approach is to divide the resin upon which the oligonucleotides are synthesized into equivalent portions and then couple each aliquot to a different substrate to create a degenerate position. After this coupling, the resin aliquots are recombined and the procedure is repeated for each degenerate position This approach results in approximately equivalent representation of each different substrate at the degenerate position. Alternatively, a mixture of different substrates can be added to a coupling step to create a degenerate position. However, different substrates have different coupling efficiencies and therefore if equal amounts of each substrate are used, each substrate may not be equivalently represented at the degenerate position. The different coupling efficiencies of different substrates can be compensated for by using a "weighted" mixture of substrates at a coupling step, wherein substrates with lower coupling efficiencies are present in greater abundance than substrates with higher coupling efficiencies.

An alternative type of oriented degenerate substrate libraries which can be used in the method of the invention is a solid-support bound substrate library. The term "solid-support bound substrate library" is intended to mean a population of substrate compounds which are connected to a solid support such as a bead or plastic pin. For general descriptions of the construction of solid-support bound libraries see for example Geysen, H. M., et al. (1986) *Mol. Immunol.* 23:709–715; Lam, K. S., et al. (1991) *Nature* 354:82–84; and Pinilla, C., et al. (1992) *BioTechniques* 13:901–905. For this type of library, the substrates are synthesized attached to the solid support, such as a bead, and degenerate positions are created by splitting the population of beads, coupling different substrates to different subpopulations and recombining the beads. The final product is a population of beads each carrying many copies of a single unique substrate. Thus, this approach has been termed "one bead/one peptide".

Act The diversity of the substrate library (e.g., the number of different substrates contained within the library) is a function of the number of degenerate residues: the greater the number of degenerate residues the greater the diversity. For example, a library in which only 2 positions are degenerate and, for example any of twenty substrates can be at these degenerate positions would represent 400 unique oligonucleotides, for example.

The reactions of the present invention may be performed under a wide range of conditions, though it will be understood that the solvents and temperature ranges recited herein are not limiting and only correspond to a preferred mode of the process of the invention.

In general, it is desirable that reactions are run using mild conditions that will not adversely affect the starting materials, the intermediates, the resin, the linker, the activated resin, the linker group or the products. For example, the reaction temperature influences the speed of the reaction, as well as the stability of the reactants and the activated resin. The reactions will usually be run at temperatures in the range of −78° C. to 100° C., more preferably in the range −20° C. to 50° C. and still more preferably in the range −20° C. to 25° C.

In general, the reactions according to the invention will be performed in a liquid medium, e.g., in a suspension of an activated solid support in a liquid medium. The reactions may be run in an inert solvent, preferably one in which the reaction ingredients, optionally including the polymeric support, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. The reactions can be conducted under anhydrous conditions, and in certain embodiments it is preferable to perform the reactions under an inert atmosphere of a gas such as nitrogen or argon.

The progress of the reaction can be monitored by techniques known to one of ordinary skill in the art. For example, aliquots of the reaction mixture can be taken at intervals and the aliquots tested, e.g., by cleavage of compounds from the solid activated support followed by spectroscopic analysis of the crude reaction mixture. Alternatively, the reaction can be monitored by chromatographic techniques such as thin-layer chromatography (TLC) or HPLC. Additionally, the disappearance of a reactant or reacts can also be monitored by techniques known to a person skilled in the art.

In certain embodiments, the methods for preparing compounds include the further step of purifying the compounds. Purity of the reaction products can be determined according to known techniques. If the products are impure, they can be determined according to known techniques. If the products are impure, they can be purified according to a variety of methods known in the art. For example, compounds immobilized on a solid support can be separated from some impurities by simple filtration and washing of the solid support to remove soluble impurities. Compounds which are not immobilized on solid supports can be purified by methods including crystallization (where the compound is crystalline), trituration, distillation, and chromatographic techniques such as TLC and HPLC (analytical or preparative scale), flash chromatography, and the like. The selection of methods for purifying compounds will be routine for the ordinarily skilled artisan.

In preferred embodiments, the purity of a compound produced according to the methods of the invention is at least about 50%, more preferably at least about 70%, still more preferably at least about 90%, and most preferably at least about 95% and still most preferably at least about 99%.

The synthesis of combinatorial libraries is well known in the art and has been reviewed (see, e.g., E. M. Gordon et al., *J. Med. Chem.* 37:1385–1401 (1994)). Thus, the subject invention contemplates methods for synthesis of combinatorial libraries of substrates described above, e.g., oligonucleotides. Such libraries can be synthesized according to a variety of methods. For example, a "split-pool" strategy can be implemented in the following way: beads of a functionalized (activated, e.g. phosphitylated) polymeric solid support are placed in a plurality of reaction vessels. To each aliquot of beads is added a solution of a different substrate bearing a reactive nucleophilic group, and the reactions proceed to yield a plurality of immobilized substrates. The aliquots of derivatized beads are then washed, "pooled" (i.e., recombined), and the pool of beads is again divided, with each aliquot being placed in a separate reaction vessel. To each reaction vessel is added a solution for deprotecting protected nucleophilic groups followed by treatment with a phosphitylation agent. The phosphitylated substrate is then treated with one or more substrates bearing reactive nucleophilic groups. The process is repeated for a predetermined number of cycles. The library of immobilized compounds can then be washed to remove impurities. In certain embodiments, the products can further be treated (e.g., cleavage) to yield hydrolyzed products.

Alternatively, a "split-pool" strategy can be implemented in the following way: a phosphitylating agent is combined with different substrates having reactive nucleophilic groups and nucleophilic groups protected by removable protecting groups. The resultant phosphitylated substrates are contacted with a polymeric solid support and are placed in a plurality of reaction vessels. To each aliquot of beads is added a solution which deprotects the protected nucleophilic group and the reactions proceed to yield a plurality of immobilized substrates. The aliquots of derivatized beads are then washed, "pooled" (i.e., recombined), and the pool of beads is again divided, with each aliquot being placed in a separate reaction vessel. To each reaction vessel is added a phosphitylated substrate. The resultant phosphitylated substrate is then treated with a solution to remove the protecting groups and the cycle can be repeated. The library of immobilized compounds can then be washed to remove impurities. In certain embodiments, the products can further be treated (e.g., cleavage) to yield hydrolyzed products.

Additionally the phosphitylated products or substrates can be oxidized to form pentavalent phosphorous groups, e.g., phophotriesters. The oxidation is normally carried out using iodine as an oxidizing agent using standard procedures. Alternatively, the oxidation can also be accomplished by reaction with peroxides like tertiary butyl peroxide and benzoyl peroxide as well as hydroperoxides. Generally, oxidation reactions should be effected before further condensation reactions between substrates are attempted to obtain best yields. Deferring oxidation until after all condensation reactions are complete may result in reduced yield of products, such as oligonucleotides, due to formation of side products or incomplete oxidation of the phosphorous group.

In another illustrative method of combinatorial synthesis, a "diversomer library" is created by the method of Hobbs, DeWitt et al. (*Proc. Natl. Acad. Sci. U.S.A.* 90:6909 (1993)).

Other synthesis methods, including the "tea-bag" technique of Houghten (see, e.g., Houghten et al., *Nature* 354:84–86 (1991)) can also be used to synthesize libraries of compounds according to the subject invention.

Combinatorial libraries can be screened to determine whether any members of the library have a desired activity, and, if so, to identify the active species. Methods of screening combinatorial libraries have been described (see, e.g., Gordon et al., *J Med. Chem., op. cit.*). Soluble compound libraries can be screened by affinity chromatography with an appropriate receptor to isolate ligands for the receptor, followed by identification of the isolated ligands by conventional techniques (e.g., mass spectrometry, NMR, and the like). Immobilized compounds can be screened by contacting the compounds with a soluble receptor; preferably, the soluble receptor is conjugated to a label (e.g., fluorophores, colorimetric enzymes, radioisotopes, luminescent compounds, and the like) that can be detected to indicate ligand binding. Alternatively, immobilized compounds can be selectively released and allowed to diffuse through a membrane to interact with a receptor. Exemplary assays useful for screening the libraries of the invention are known in the art (see, e.g., E. M. Gordon et al., *J. Med. Chem.* 37:1385–1401 (1994)).

Combinatorial libraries of compounds can also be synthesized with "tags" to encode the identity of each member of the library (see, e.g., W. C. Still et al., U.S. Pat. No. 5,565,324 and PCT Publication No. WO 94/08051). In general, this method features the use of inert, but readily detectable, tags, that are attached to the solid support or to the compounds. When an active compound is detected (e.g., by one of the techniques described above), the identity of the compound is determined by identification of the unique accompanying tag. This tagging method permits the synthesis of large libraries of compounds which can be identified at very low levels.

In preferred embodiments, the libraries of compounds of the invention contain at least 30 compounds, more preferably at least 100 compounds, and still more a preferably at least 500 compounds. In preferred embodiments, the libraries of compounds of the invention contain fewer than 109 compounds, more preferably fewer than $10^8$ compounds, and still more preferably fewer than $10^7$ compounds.

A library of compounds is preferably substantially pure, i.e., substantially free of compounds other than the intended products, e.g., members of the library. In preferred embodiments, the purity of a library produced according to the methods of the invention is at least about 50%, more preferably at least about 70%, still more preferably at least about 90%, and most preferably at least about 95%.

The libraries of the invention can be prepared according to the methods of the invention.

Libraries of the invention are useful, e.g., for drug discovery. For example, a library of the invention can be screened (e.g., according to the methods described herein) to determine whether the library includes compounds having a pre-selected activity. Thus, for example, a library can be screened to determine whether compounds of the library have anti-bacterial activity or any other activity which can be detected in vitro or in vivo, e.g., anti-inflammatory activity, enzyme inhibitory activity, and the like.

EXAMPLES

Example 1: Novel Phosphodiester Synthesis

Novel chemistries for phosphodiester synthesis were developed to reduce the cost of large scale synthesis and to increase the flexibility for oligomer labeling and library synthesis. The process involves the use of phosphitylating agents for the condensation of two nucleophilic moieties to generate a protected phosphite linkage. Facile oxidation of the phosphite gives ready access to the phosphate.

Phosphitylation of either the 3' or the 5' hydroxyl of a deoxynucleoside, followed by the addition of another nucleoside and oxidation gives a protected dinucleotide. Repetitive synthesis allows chain extension in either the 3' to 5' direction or the 5' to 3' direction depending on the original deoxynucleoside used. The final step in the 5' to 3' synthesis is de-protection of the 3' hydroxyl of the oligonucleotide, allowing 3' functionalization while still on the solid support.

In situ phosphoramidite formation provides for synthetic manipulations that are not possible with preformed phosphoramidites. The basic units of DNA synthesis, the nucleotides, can be replaced with pre-formed oligonucleotide blocks. Phosphitylation of one unprotected end of the block, followed by coupling to an oligo on a solid support extends the polynulcleotide in blocks of nucleotides. This single strand ligation of protected DNA fragments on solid supports leads to blocks of pre-synthesized oligomers and facilitates allows synthesis of oligo libraries with fixed and variable region sequences.

The approaches to the chemical preparation of phosphates can be applied to a variety of phosphate esters. Combinatorial synthesis of phosphate esters will be valuable in screening for transition state analogue inhibitors of esterases and proteases or for phospholipids with novel physical or biological properties.

These chemistries can be tailored to achieve the needs of industry where specific variable and non-variable regions of DNA need to be constructed in specific orientations for recombination into expression systems to study expression of genomic sequences.

In this example, the objective was to synthesize 70 mer oligonucleotides that have a common 50 mer region and a variable 20 mer region on the 3' end.

Experimental Design

1) Reverse Construction 3' phosphoramidites are synthesized in situ from the 3' nucleoside, and then a large pool of the 50 mer is synthesized from 5' to 3' on the solid support. The solid support is then split, repackaged and synthesis then continues on the smaller columns in the 5' to 3' direction.

2) Single Strand Ligation Chemical ligation of two single strands of DNA by conversion of the 50 mer to an activated phosphoramidite that may be added to the 20 mer on the column as the final synthesis step.

Reverse Construction for Synthesis of 70 mer Oligonucleotides

3' phosphoramidites are synthesized in situ from the 3' nucleoside, and then a large pool of the 50 mer is synthesized from 5' to 3' on the solid support. The solid support is then split, re-packaged and synthesis then continues on the smaller columns in the 5' to 3' direction.

A 22 mer with an Afl 11 site was synthesized using in situ 3' amidites. The complement to the sequence was also synthesized using 3' amidites. Controls using standard amidites synthesized in the 3' to 5' direction were used. The oligos were analyzed by:
 i) PAGE
 ii) Hybridization
 iii) Restriction enzyme Hfa 11 analysis The results of the analysis showed that sequences of the correct length were present in both the control and 5' to 3' sequences, and that the control had incomplete digestion with Afl 11 and the reverse oligos showed partial digestion with Afl 11 suggesting incomplete de-protection.

Single Strand Ligation for Synthesis of 70 mer Oligonucleotides

The chemical ligation of two single strands of DNA by conversion of the 50 mer to an activated phosphoramidite that can be added to a solid support linked 20 mer on the column as the last synthesis step has been performed. A pentamer of poly T's was synthesized, activated and conjugated to a pentamer of poly T on a column, cleaved, deprotected and analyzed on ion exchange HPLC. The chromatogram is shown in FIG. 1.

Example 2: Novel Approach to Phosphite and Phosphate Synthesis

This example shows a novel approach to phosphite and phosphate synthesis using inexpensive phosphoramidites adapted to facile automation. The process applies PCN and analogous phosphitylating agents to affect condensation of nucleophilic moieties producing a protected phosphite linkage between them. This approach can be used to assemble libraries of phosphites. Facile oxidation of phosphite then gives ready access to phosphates. The use of this process is best exemplified by the preparation of oligonucleotides.

Figure 2:
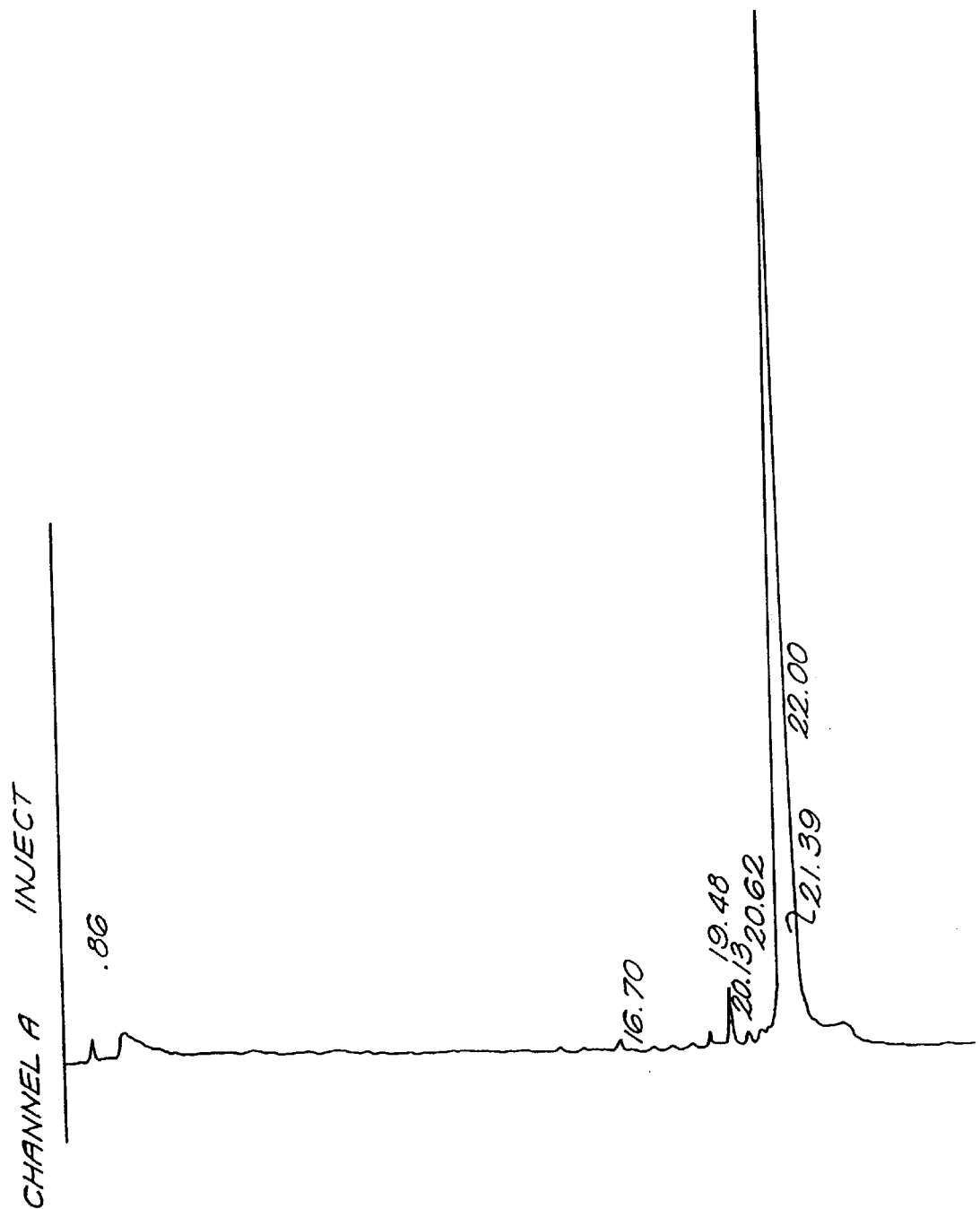
FIG. 2 is an anion exchange chromatogram of an $S_{22}$ oligonucleotide made using conventional DNA synthesis chemistry, as detailed in Example 3.

Stepwise phosphitylation of either the 3' or the S' hydroxyl of a deoxynucleoside with PCN followed by addition of a nucleoside and oxidation of the resulting dinucleoside phosphite to a protected phosphate gives a protected dinucleotide. Repeating the process allows chain extension in either the customary 3' to 5' direction or the reverse, extension in the S' to 3' direction (FIG. 2). The latter allows easy labeling and or other modification of the 3' end of the target oligonucleotide.

Figure 3:
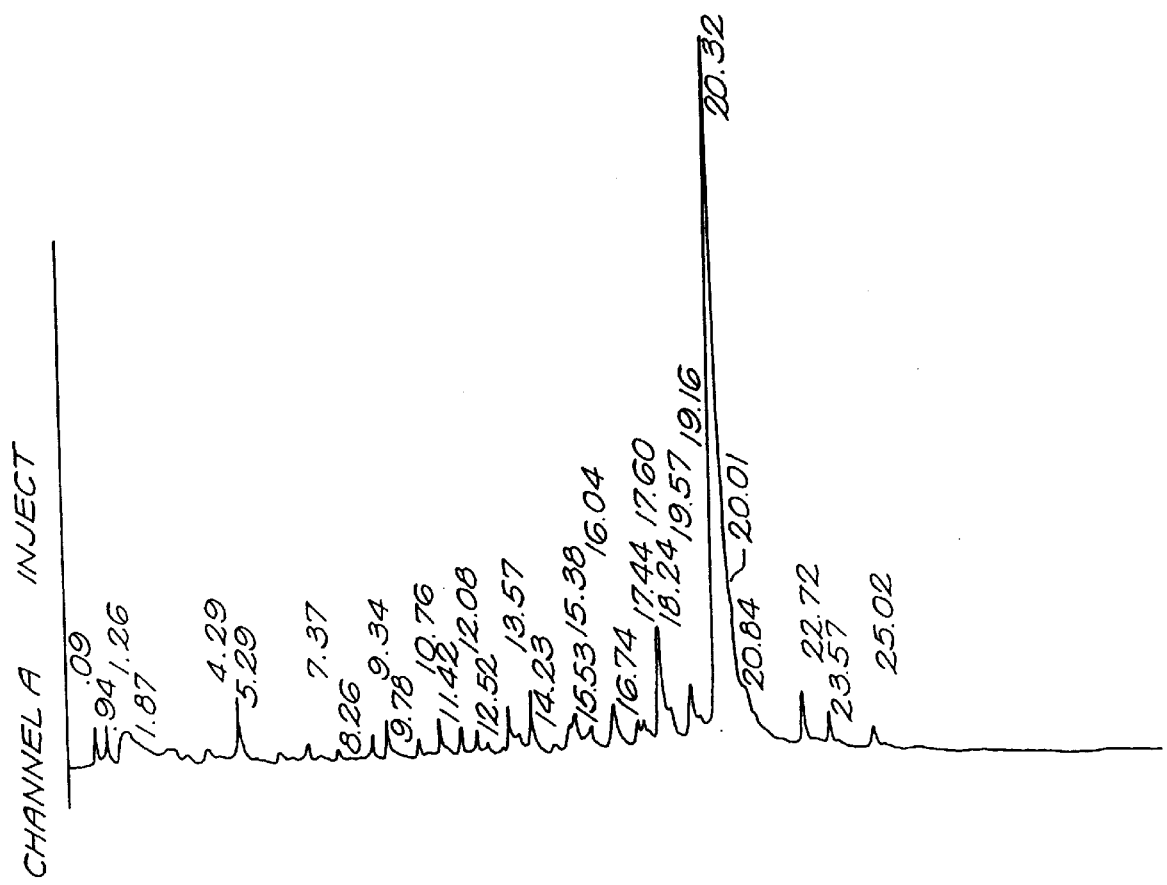
FIG. 3 is an anion exchange chromatogram of a $C_{22}$ oligonucleotide made using 3' to 5' "P-LINK" chemistry, as detailed in Example 3.

The formation in situ of activated phosphoramidites allows condensation of nucleophile blocks consisting of preformed oligonucleotides. Thus, chain extension can proceed many bases at a time. This amounts to a chemical ligation of single-stranded DNA fragments into oligonucleotides larger than can normally be prepared on a solid support. In addition, the preparation of repeat sequences and oligonucleotide libraries containing variable blocks is greatly facilitated (FIG. 3).

Chemical libraries derived from the in situ coupling process described are not limited to oligonucleotides. Construction is possible of di- and trialkyl phosphite compounds. Through treatment with oxidizing agents, alkyl phosphates are also achievable. Treatment with organosulfur reagents results in formation of thiophosphates tetrahedral species whose conformational stability allows the resolution of thiophosphate enantiomers. Large libraries of phospholipids can be prepared by phosphitylation of diglycerides followed by reaction with alcohols and oxidation to give phosphoglycerides (Scheme 1).

Scheme 1

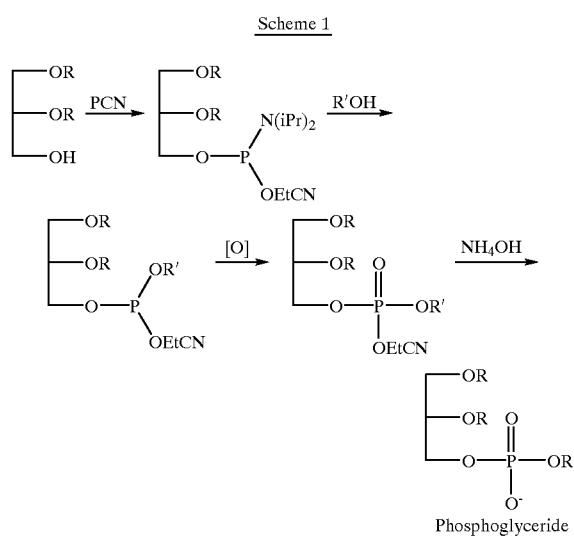

Combinatorial synthesis of phosphites is readily adaptable to solid supported techniques through standard linkers to the moieties being condensed or alternatively, the phosphoramidite can be attached to the support, the synthesis proceed to give trialkylphosphites, and the cleavage step will then release the phosphate (Scheme 2).

Scheme 2

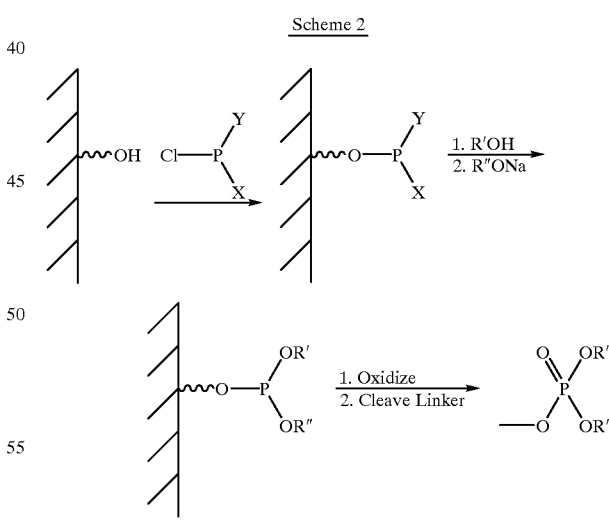

The phosphitylating agents that make this process possible are phosphoramidites such as PCN-stable solids which cleanly add nucleophilic species under weak acid catalysis with loss of diisopropyl amine. N,N-dialkylaminophosphoramidites were first used to prepare stable nucleoside phosphites for use in oligonudeotide synthesis (Beaucage et al. *Tetrahedron Lett.* (81) 22 1859). The preparation of nucleoside phosphoramidites was improved and used in solid-supported synthesis (Beaucage, *Tetrahedron Lett.* (84) 25 375). Several attempts at the use of in situ phosphite formation have relied on highly reactive halophosphites (Jayaraman and McClaugherty *Tetrahedron Lett.* (82) 23 5377; Fourrey and Varenne *Tetrahedron Lett.* (83) 24 1963; Cau et al. *Tetrahedron Lett.* (83) 24 1019). The process of in situ activation has been initially demonstrated by Barone et al. (*Nucleic Acids Research* (84)12 4051) for standard 3' to 5' oligonucleotide synthesis.

Example 3: "P-LINK" Chemistry for Oligonucleotide Synthesis

The synthesis of oligonucleotides, as developed by Caruthers (Matteucci, M. D.; Caruthers, M. II. *J. Am. Chem. Soc.,* 1981, 103, 3185) and Köoster (Sinah, N. D.; Biernat, J.; McManus, J.; Köster, H. *Nucleic Acid Res.,* 1984, 12, 4539), has become an established commercial endeavor. An alternative approach to the standard process has been developed and is described herein, employing the present invention ("P-LINK", Chemicus, Inc.), which compares favorably to the use of commercial phosphoramidites. Complimentary pairs of a 22-base pair oligonucleotide, with a strategically located EcoR1 cleavage site, were prepared using commercial phosphoramidites in the standard 3' to 5' direction on an automated instrument. The same sequences were prepared using P-LINK chemistry. In this approach, protected nucleosides are converted to active synthons prior to their introduction onto the automated instrument. Via this approach, the complimentary pairs were prepared in both the 3' to 5' direction and the 5' to 3' suitability of these oligos for molecular biology was demonstrated by successful radiolabelling, hybridization and EcoR1 cleavage. In all three cases, results are fully consistent with oligonucleotides prepared by established methods.

Examples of the Application

Oligonucleotide Synthesis

This study compared the synthesis of two model oligonucleotides by three synthetic processes. All syntheses were performed on a commercial DNA synthesizer (Millipore) at scales of 100 nMol up to 250 nMol using flow-through columns filled with derivatized 500Å controlled pore glass (CPG) as specified in the experimental section below.

Test Sequences

Two complimentary oligonucleotides were designed which contain the restriction sites (↓) for EcoR1 endonuclease.

↓
(C22–) 5'-TGT CAG TGA CTG TGA ATT CGC T-3'
(SEQ ID NO:1) (Samples 1,3 & 5)
(S22–) 5'-AGC GAA TTC ACA GTC ACT GAC A-3'
(SEQ ID NO:2) (Samples 2,4 & 6)

Synthesis by Standard Method

In a typical experiment, the synthesis is performed automatically using the chemistries and the standard protocols as specified by the instrument manufacturer. The column is packed with 5–7 mg of CPG (typ. 35 µmol/g; Chemgenes) derivatized through the 3'-hydroxyl of the appropriate 5'-dimethoxytrityl (DMT) protected deoxyribonucleotide cyanoethyl-phosphoramidite. Synthesis is performed sequentially from the 3' to 5' end by addition of the appropriate 5'-DMT protected phosphoramidites (0.1M in acetonitrile, Applied Biosystems) following the standard procedures.

The completed oligonucleotide is cleaved from the CPG support and deprotected by treating with aqueous ammonium hydroxide at 60° C. overnight (>8 hr) and drying under vacuum. The oligonucleotide is then dissolved in 500 µl of HPLC grade water and analyzed by anion exchange HPLC (Waters) using standard buffers and gradient as specified by the manufacturer. FIGS. 1 and 2 show the chromatograms for these oligonucleotides; (labelled as samples 1 and 2, respectively).

3' to 5' Synthesis by P-LINK Method

In a typical experiment, the 5'-dimethoxytrityl protected deoxyribonucleotide cyanoethylphosphoramidites (phosphoramidites) are prepared from the corresponding 5'-dimethoxytrityl protected deoxyribonucleosides (Chemgenes) by reaction with 1.5 equivalents of 2-cyanoethyl-N,N,N',N'-tetraisopropylaminophosphane (PCN, Chemgenes) and 1.0 equivalents of tetrazole (Chemgenes) in 25% dimethylformamide (DMF)/acetonitrile (ACN) at 240 for 90 minutes. Conversion efficiency is analyzed by C18 reverse phase HPLC (Waters) using an isocratic mixture of 90% ACN/10% water.

Synthesis is performed automatically using 0.12M solutions of the P-LINK prepared phosphoramidites and using the other standard reagents and instrument protocol as above. The column is packed with 5–7 mg of the appropriately derivatized CPG (typ. 35 µmol/g, Chemgenes). Synthesis is performed sequentially from the 3' to 5' end by addition of the appropriate 5'-DMT protected phosphoramidites following the standard procedures.

Figure 4:
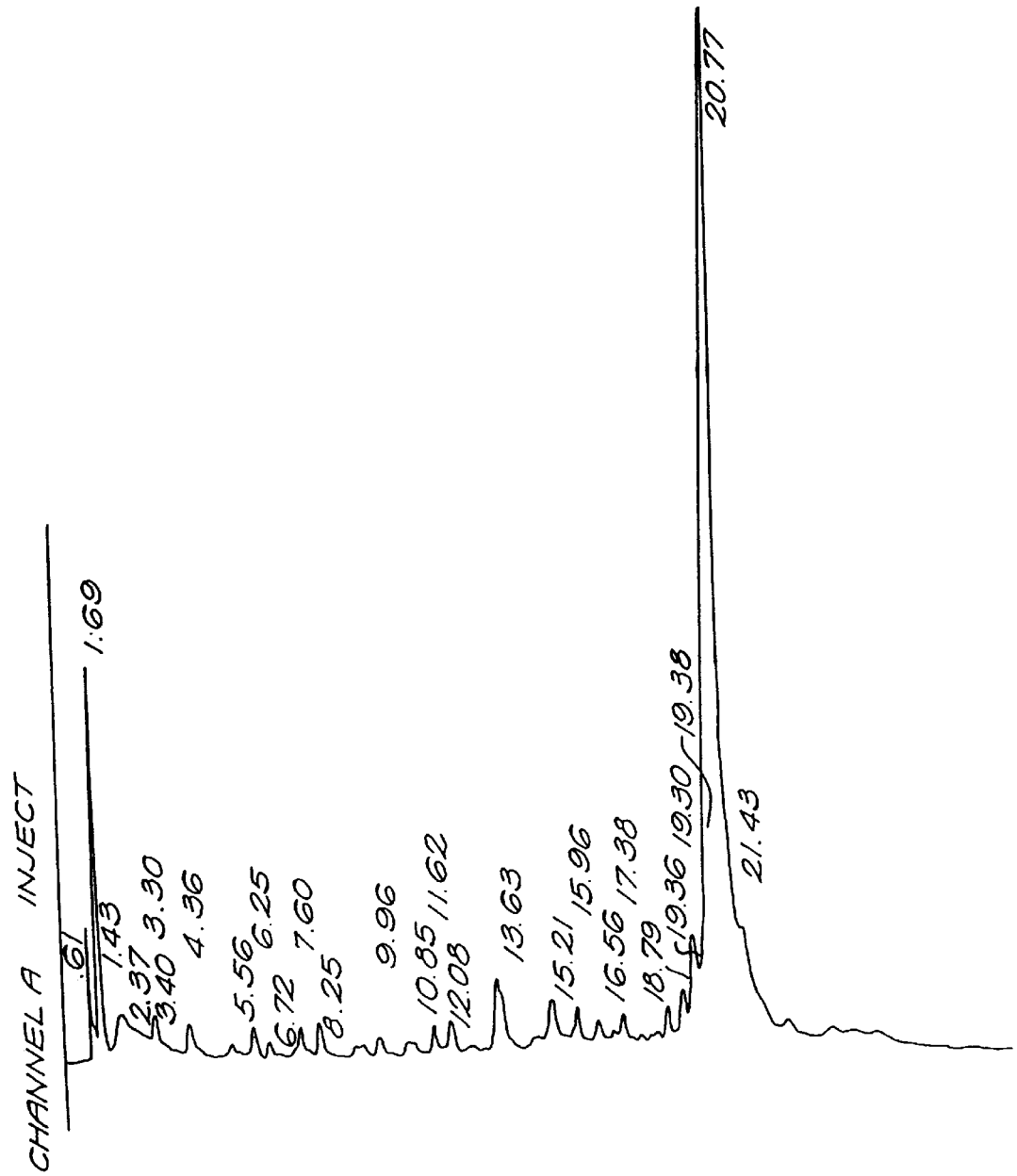
FIG. 4 is an anion exchange chromatogram of an $S_{22}$ oligonucleotide made using 3' to 5' "P-LINK" chemistry, as detailed in Example 3.

The completed oligonucleotide is cleaved from the CPG support and deprotected by treating with aqueous ammonium hydroxide at 60° C. overnight (>8 hr) and drying under vacuum. The oligonucleotide is then dissolved in 500 µl of HPLC grade water and analyzed by anion exchange HPLC (Waters) using standard buffers and gradient as specified by the manufacturer. FIGS. 3 and 4 show the chromatograms for these oligonucleotides; (labelled as samples 3 and 4, respectively).

5' to 3' Synthesis by P-LINK Method

In a typical experiment, the 3'-dimethoxytrityl protected deoxyribonucleotide cyanoethylphosphoramidites (phosphoramidites) are prepared from the corresponding 3'-dimethoxytrityl protected deoxyribonucleosides (Chemgenes) by reaction with 1.5 equivalents of 2-cyanoethyl-N,N,N',N'-tetraisopropylaminophosphane (PCN, Chemgenes) and 1.0 equivalents of tetrazole (Chemgenes) in 25% dimethylformamide (DMF)/acetonitrile (ACN) at 240 for 90 minutes. Conversion efficiency is analyzed by C18 reserve phase HPLC (Waters) using an isocratic mixture of 90% ACN/10% water.

Synthesis is performed automatically using 0.12M solutions of the P-LINK prepared phosphoramidites with the other standard reagents as above. For the reverse synthesis runs, the instrument protocol was modified to extend the DMT deprotection step by 30%. The column is packed with 5–7 mg of CPG (typ. 30 µmol/g; Chemgenes) derivatized through the 5'-hydroxyl of the appropriate 3'-dimethoxytrityl protected deoxyribonucleotide cyanoethylphosphoramidite. Synthesis is performed sequentially from the 5' to 3' end by addition o the appropriate 3'-DMT protected phosphoramidites following the standard procedures.

Figure 5:
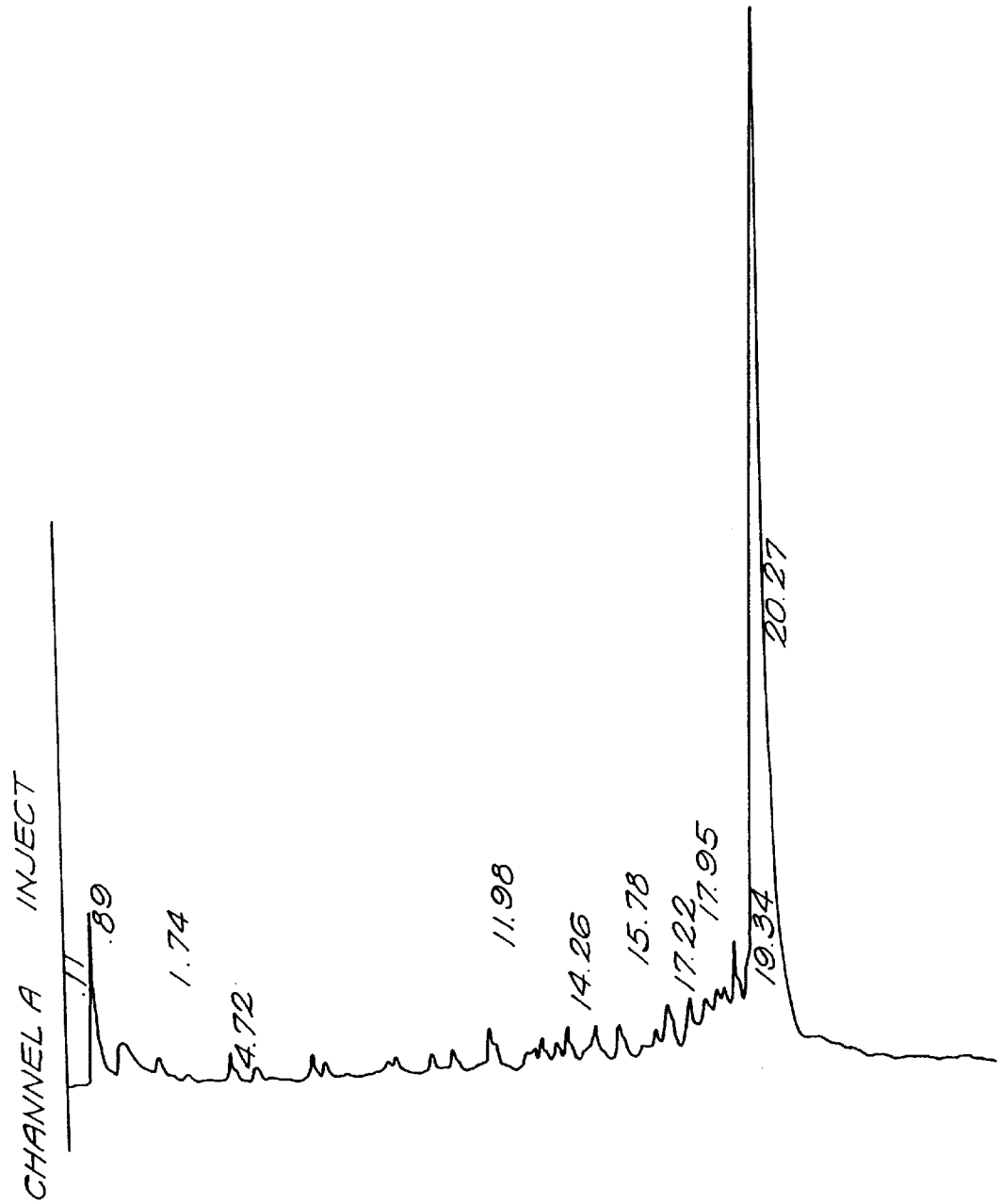
FIG. 5 is an anion exchange chromatogram of a $C_{22}$ oligonucleotide made using 5' to 3' "P-LINK" chemistry, as detailed in Example 3.
Figure 6:
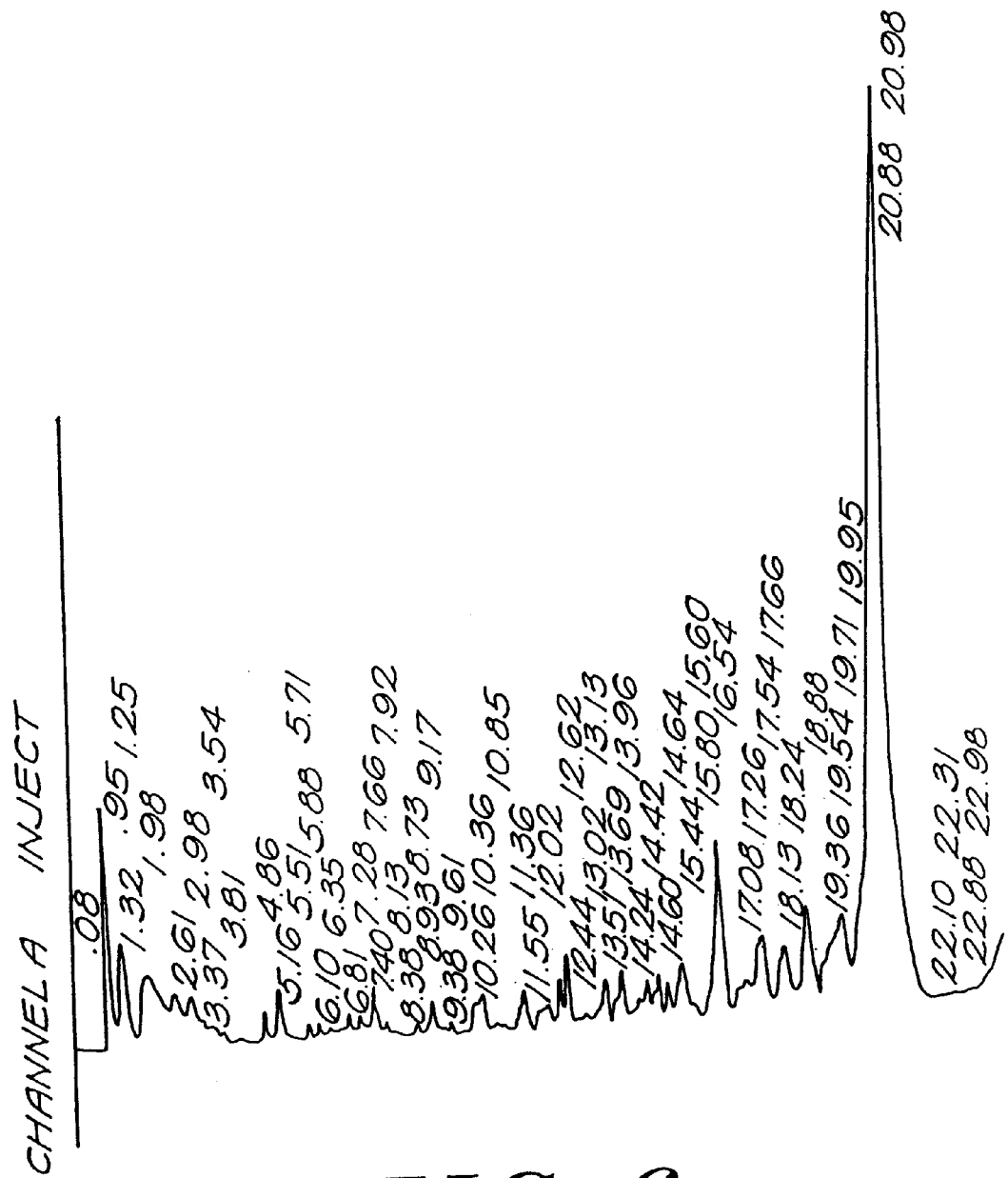
FIG. 6 is an anion exchange chromatogram of an $S_{22}$ oligonucleotide made using 5' to 3' "P-LINK" chemistry, as detailed in Example 3.

The completed oligonucleotide is cleaved from the CPG support and deprotected by treating with aqueous ammonium hydroxide at 60° C. overnight (>8 hr) and drying under vacuum. The oligonucleotide is then dissolved in 500 µl of HPLC grade water and analyzed by anion exchange HPLC (Waters) using standard buffers and gradient as specified by the manufacturer. FIGS. 5 and 6 show the chromatograms for these oligonucleotides; (Labelled as samples 5 and 6, respectively).

Analytical Results

Synthetic oligonucleotides were analyzed by anion chromatography as shown in FIGS. 1 through 6. In addition, the six synthetic oligonucleotides and a synthetic standard 24 mer (BCMP 206) were analyzed by a set of procedures designed to test and compare the products prepared by the alternative methods. The 5'-end of all oligonucleotides were radiolabelled with $\gamma$-$^{32}$P phosphate using $\gamma$-$^{32}$P ATP and T4 polynucleotide kinase. The labelled products (2 ml) were spotted on DE81 filter paper, washed 3 times with ammonium formate (10 min each time), washed once with ethanol, and counted. In most cases 1–2 million counts per minute (CPM) were detected for the samples. Oligonucleotide 2 and the standard 24-mer were each about 600,000 CPM.

Pairs of radiolabelled oligonucleotide samples were mixed and annealed to form double stranded DNA which was suitable for subsequent cleavage at the EcoR1 restriction site. An isotope dilution procedure was used to equalize the concentration and radioactivity levels for each oligonucleotide in the pair. The 10× annealing buffer was 500 mM Tris-HC (pH 7.5), 1000 mM NaCL. Solutions were prepared, heated to 90° C. for 5 min, centrifuged and allowed to cool slowly to ambient temperature over 2 hr. The pairings were as follows: 1+2,3+4,5+6,+4,2+3,1+6 and 2+5. The annealed pairs were digested with EcoR1 according to the following recipe: annealed oligo (80 μl), 1M DTT (0.8 μl), 1M MgCl$_2$ (0.8 μl), BSA (50 mg/μl), EcoR1 (1 μl at 20 μ/μl, Amersham). The digestions were incubated at 37° C. for 2 hr and allowed to cool to ambient temperature overnight.

Figure 7:
FIG. 7 is an autoradiogram comparing the oligonucleotides depicted in FIGS. 1–6.
Figure 8:
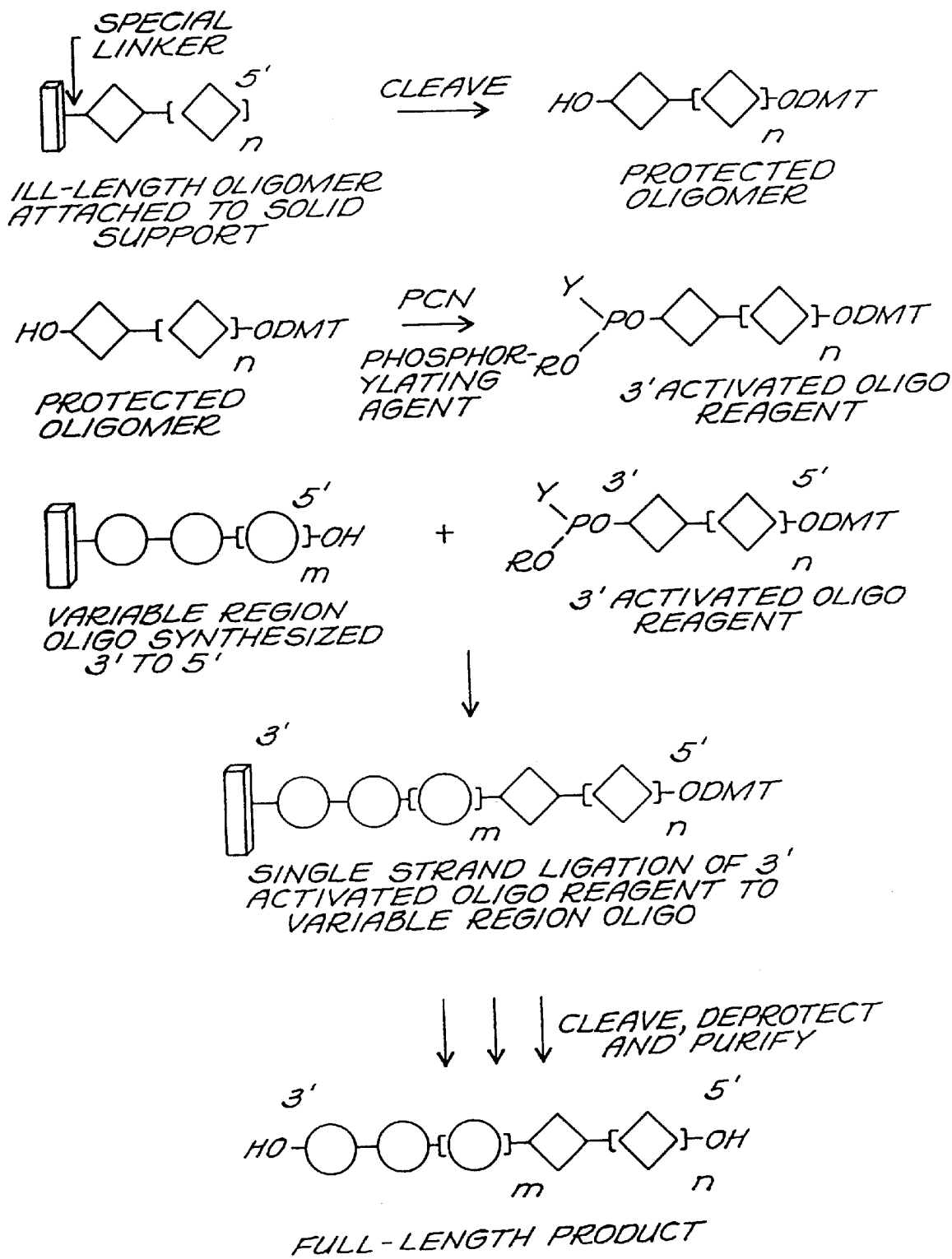
FIGS. 8 and 9 graphically illustrate single strand ligation of oligomers using the chemistries of the present invention.
Figure 9:
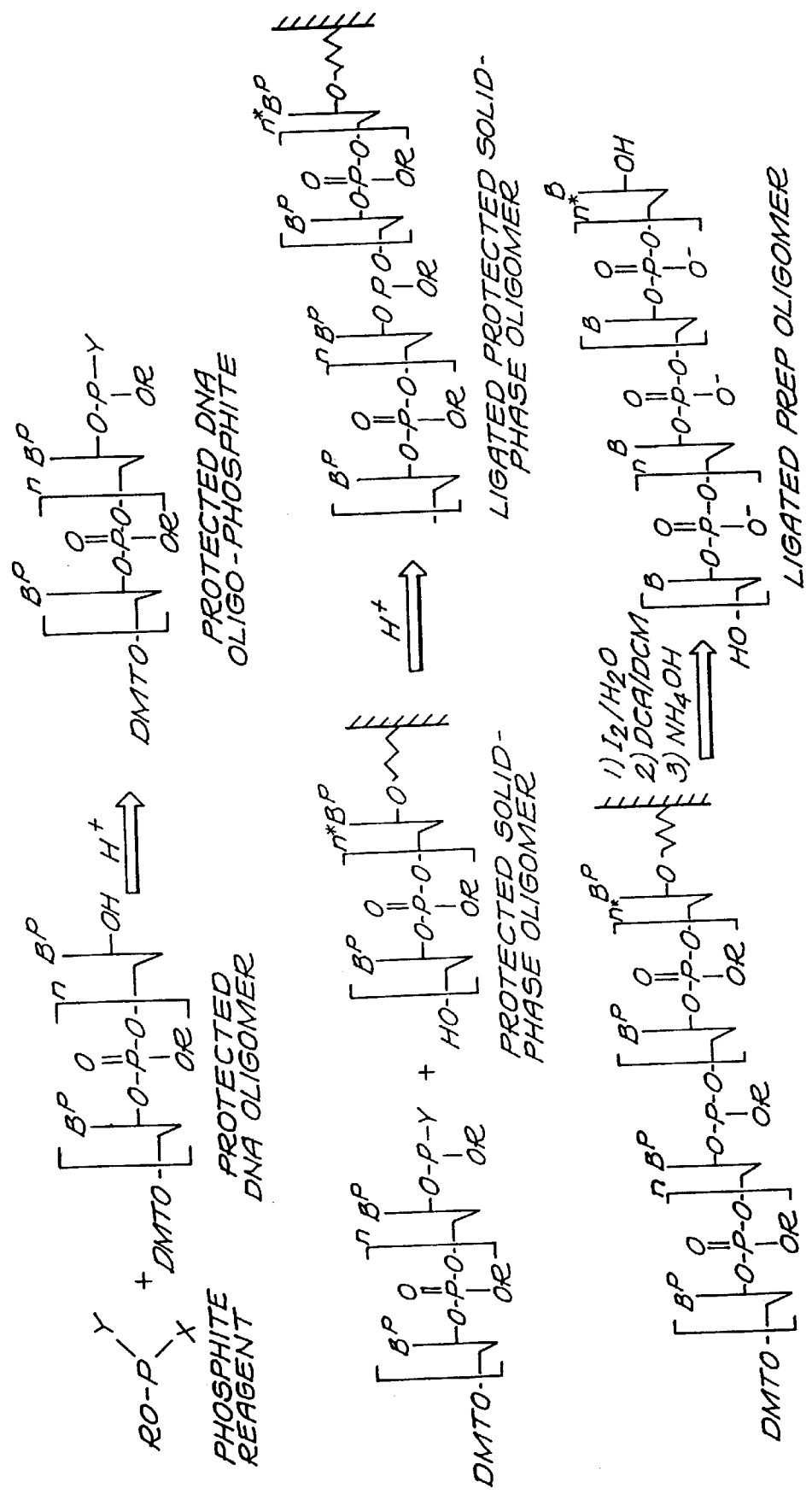
Figure 10:
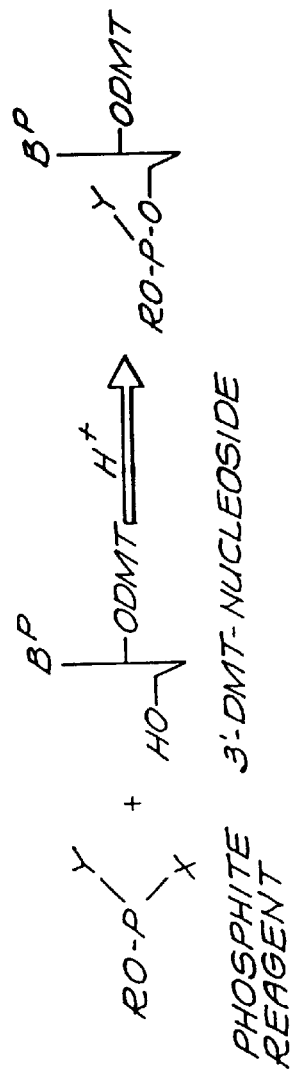
FIGS. 10 and 11 graphically illustrate double strand ligation of oligomers using the chemistries of the present invention.
Figure 10:
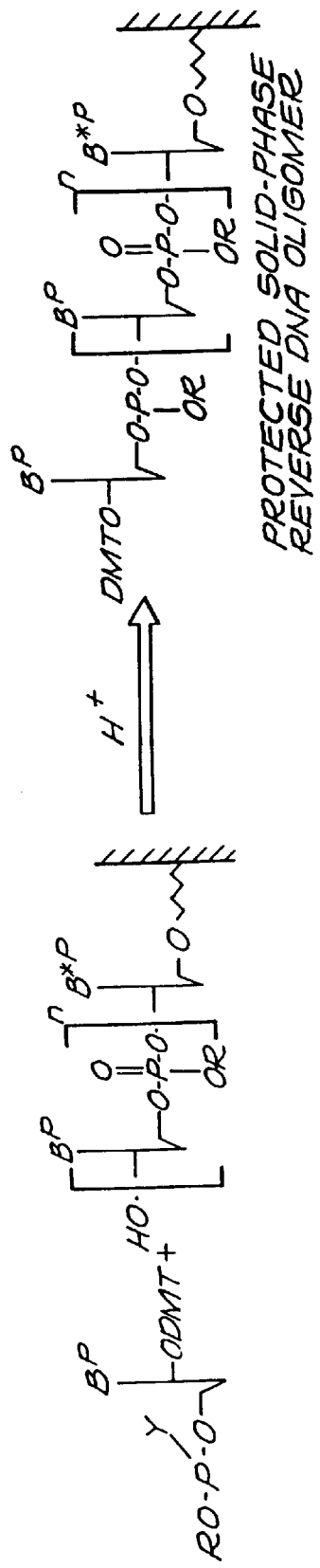
Figure 10:
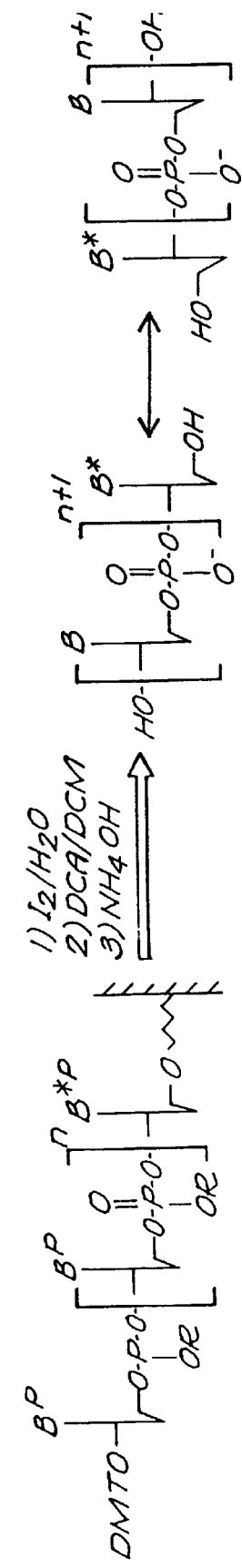
Figure 11:
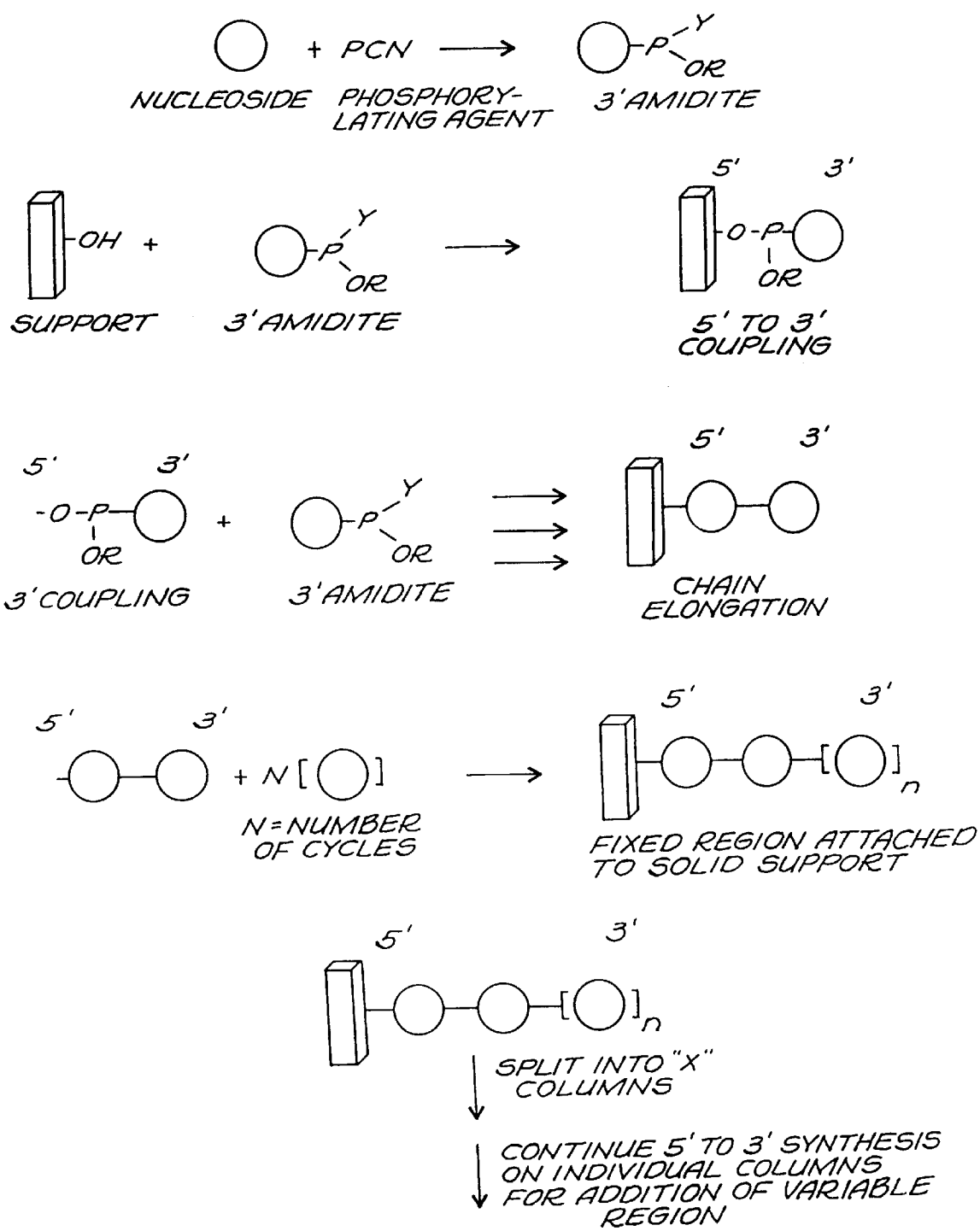

The digested DNA was denatured by adding an equal volume of formamide/dye solution and heating the solution to 90° C. for 6 min, and were analyzed by gel electrophoresis using standard methods. FIG. 7 is an audioradiogram of the gel and is evidence that the oligonucleotides synthesized with the P-LINK chemistry are identical to oligonucleotides synthesized by conventional methods.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims. The contents of all references, pending patent applications and issued patents cited throughout all portions of this application including the background are expressly incorporated by reference.

What is claimed is:

1. A method for preparing organic moieties, comprising the steps of:
    a) combining a substrate having a reactive nucleophilic group and a nucleophilic group protected by a removable protecting group, with a phosphitylating agent, thereby forming an in situ phosphitylated substrate;
    b) combining said in situ phosphitylated substrate of step a) with a functionalized support, such that an in situ phosphitylated substrate is bound to said support, thereby forming a support bound phosphitylated substrate.

wherein said substrate contains at least two different nucleophilic groups.

2. The method of claim 1, further comprising the step of:
    c) treating said support bound phosphitylated substrate of step b) to selectively remove said protecting group from said protected nucleophilic group, thereby forming a support bound phosphitylated substrate bearing a reactive nucleophilic group.

3. The method of claim 2, further including the step of capping failure substrates by reacting a capping agent with reactive nucleophilic groups of failure substrates.

4. The method of claim 1, wherein said substrate contains an amino group and a hydroxyl group.

5. The method of claim 4, wherein said hydroxyl group is protected by a protecting group.

6. The method of claim 1, wherein said substrate contains two amino groups.

7. The method of claim 6, wherein one amino group is protected by a protecting group.

8. The method of claim 1, wherein said substrate contains at least two nucleophilic groups selected from the group consisting of amino groups, thiol groups, hydroxyl groups and phosphorous groups.

9. The method of claim 1, wherein said phosphitylating agent has the formula:

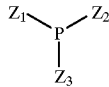

wherein one of $Z_1$, $Z_2$ and $Z_3$ is displaced by said reactive nucleophilic group of said substrate, and wherein $Z_1$ is chlorine, $Z_2$ is an N,N-dimethylamino, diethylamino, diisopropylamino, or N-morpholino group and $Z_3$ is a β-cyanoethyl group.

10. An automated method for preparing organic moieties, comprising the steps of:
  a) treating a support with a phosphitylating agent, thereby forming an a catena phosphitylated support;
  b) treating said a catena phosphitylated support with a substrate having a reactive nucleophilic group and a nucleophilic group protected by a removable protecting group, thereby forming a support bound phosphitylated substrate bearing a protecting group;
  c) removing said protecting group from said support bound phosphitylated substrate, thereby forming a support bound phosphitylated substrate bearing a reactive nucleophilic group;
  d) combining a substrate having a reactive nucleophilic group and a nucleophilic group protected by a removable protecting group with a phosphitylating agent, thereby forming an in situ phosphitylated substrate; and
  e) combining said in situ phosphitylated substrate of step d) with said phosphitylated substrate bearing a hydroxyl functionality of step c), thereby forming a support bound phosphitylated substrate bearing a protecting group;
  f) removing said protecting group from said support bound phosphitylated substrate of step e), thereby forming a support bound phosphitylated.

11. The method of claim 10, wherein said substrate contains at least two different nucleophilic groups.

12. The method of claim 11, wherein said substrate contains an amino group and a hydroxyl group.

13. The method of claim 12, wherein said hydroxyl group is protected by a protecting group.

14. The method of claim 13, wherein said protecting group is a dimethoxytrityl group.

15. The method of claim 11, wherein said substrate contains two amino groups.

16. The method of claim 15, wherein one amino group is protected by a protecting group.

17. The method of claim 11, wherein said substrate contains at least two nucleophilic groups selected from the group consisting of amino groups, thiol groups, hydroxyl groups and phosphorous groups.

18. The method of claim 10, wherein said phosphitylating agent has the formula:

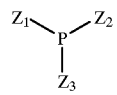

wherein one of $Z_1$, $Z_2$ and $Z_3$ is displaced by said reactive nucleophilic group of said substrate.

19. The method of claim 10, wherein $Z_1$ is chlorine, $Z_2$ is an N,N-dimethylamino, diethylamino, diisopropylamino, or N-morpholino group and $Z_3$ is a β-cyanoethyl group.

20. The method of claim 10, further including the steps of
  i) treating said support bound phosphitylated substrate bearing a reactive nucleophilic group of step c) with a phosphitylating agent, thereby forming a phosphitylated support bound substrate;
  j) treating said phosphitylated support bound substrate of step i) with a substrate having a reactive nucleophilic group and a nucleophilic group protected by a removable protecting group, thereby forming a support bound phosphitylated substrate bearing a protecting group;
  k) removing said protecting group from said support bound phosphitylated substrate of step j), thereby forming a support bound phosphitylated substrate bearing a reactive nucleophilic group; and
  l) capping failure substrates by reacting a capping agent with reactive nucleophilic groups of failure substrates.

21. The method of claim 1, wherein said support bound phosphitylated substrate of step b is an oligonucleotide comprising at least 2 nucleotides, and wherein said method further comprises reacting said support bound phosphitylated substrate of step b with a different oligonucleotide comprising at least 2 nucleotides.

22. The method of claim 1, wherein said support bound phosphitylated substrate of step b is an oligonucleotide comprising at least 20 nucleotides, and wherein said method further comprises reacting the support bound phosphitylated substrate of step b with a different oligonucleotide comprising at least 20 nucleotides.

23. The method of claim 1, wherein said support bound phosphitylated substrate of step b is a diglyceride.

24. The method of claim 23, further comprising reacting said phosphitylated substrate with one or more alcohols.

25. The method of claim 24, further comprising an oxidation step to form a phosphoglyceride.

26. The method of claim 1, wherein said phosphitylating agent is 2-cyanoethyl-N,N,N',N'-tetraisopropylaminophosphane.

* * * * *